(12) United States Patent
Schaefer

(10) Patent No.: US 6,960,266 B1
(45) Date of Patent: Nov. 1, 2005

(54) TOWELLETTES IMPREGNATED WITH A PAINT AND NAIL POLISH REMOVER FORMULATION

(75) Inventor: Bernard S. Schaefer, Richfield, WI (US)

(73) Assignee: Quick Clean Products, Inc., Hubertus, WI (US)

(*) Notice: Subject to any disclaimer, the term of this patent is extended or adjusted under 35 U.S.C. 154(b) by 71 days.

(21) Appl. No.: 10/754,281

(22) Filed: Jan. 9, 2004

(51) Int. Cl.[7] ............................................... A61K 7/00
(52) U.S. Cl. ..................... 134/38; 510/130; 510/137; 510/138; 510/438; 510/118; 424/401
(58) Field of Search ................................ 510/130, 438, 510/118, 137, 138; 424/70.12, 401; 134/42, 134/38

(56) References Cited

U.S. PATENT DOCUMENTS

| | | | |
|---|---|---|---|
| 5,965,115 A * | 10/1999 | Bolich et al. ............ 424/70.12 |
| 6,071,865 A | 6/2000 | Pickering et al. ........... 510/118 |
| 6,225,269 B1 | 5/2001 | Baker .......................... 510/118 |
| 6,432,429 B1 * | 8/2002 | Maddern et al. ............ 424/402 |
| 2002/0031486 A1 * | 3/2002 | Lunsmann et al. ...... 424/70.28 |
| 2002/0183215 A1 | 12/2002 | Berglund ..................... 510/118 |

* cited by examiner

Primary Examiner—Necholus Ogden
(74) Attorney, Agent, or Firm—Donald J. Ersler

(57) ABSTRACT

At least one towellette is impregnated with a paint and nail polish remover formulation (remover formulation) by spraying. The remover formulation cleans polyurethane paint, enamel paint, printing inks and adhesives from hands, or nail polish from finger nails. The remover formulation includes dimethyl ester, dimethyl sulfoxide and methyl soyate, which all act as solvents. Alcohol, ethyl lactate and oxy-1,2-ethanediyl nonylphenyl-omega-hydroxy are preferably included in the remover formulation. The alcohol acts as a solvent and a drying agent. The ethyl lactate acts as a solvent. The oxy-1,2-ethanediyl nonylphenyl-omega-hydroxy acts as a surfactant to remove the solvents. The remover formulation also preferably includes aloe vera, propylene glycol and water. The at least one towellette is preferably in the form of a roll, which is contained in a dispenser.

10 Claims, 2 Drawing Sheets

TOWELLETTES IMPREGNATED WITH A PAINT AND NAIL POLISH REMOVER FORMULATION

BACKGROUND OF THE INVENTION

1. Field of the Invention

The present invention relates generally to paint removers and nail polish removers and more specially to towellettes impregnated with a paint and nail polish remover formulation, which may be safely used to clean hands with paint or to remove nail polish from nails.

2. Discussion of the Prior Art

There are numerous formulations for nail polish remover that contain acetate or acetate derivative. However, there are some patents, which disclose a nail polish remover without acetate or an acetate derivative. U.S. Pat. No. 6,071,865 to Pickering et al. discloses a nail polish remover. The Pickering et al. patent includes a nail polish removing composition that includes fatty acid methyl or ethyl esters, N-Methyl-2-pyrrolidone or similar solvent, and a surfactant. U.S. Pat. No. 6,225,269 to Baker discloses a nail polish remover. The Baker patent includes a nail polish remover composition comprising aliphatic dibasic esters and alkali refined soybean oil. Patent application No. 2002/0183215 to Berglund discloses a nail polish lacquer remover. The Berglund patent includes a composition which is a mixture of a hydroxylated carboxylic acid ester and a mono-, di- or tricarboxylic acid ester for solvating a nail polish lacquer.

Accordingly, there is a clearly felt need in the art for towellettes impregnated with a paint and nail polish remover formulation, which may be safely used to clean paint, printing inks, adhesives or any other unwanted material from hands; remove nail polish from nails; and does not contain acetate or an acetate derivative.

SUMMARY OF THE INVENTION

The present invention is particularly directed to providing towellettes impregnated with a paint and nail polish remover formulation, which may be safely used to clean paint from hands or to remove nail polish from nails. Preferably, at least one towellette is impregnated with the paint and nail polish remover formulation (remover formulation). The remover formulation cleans polyurethane paint, enamel paint, printing inks and adhesives from hands, or nail polish from finger nails.

The remover formulation includes dimethyl ester, dimethyl sulfoxide and methyl soyate, which all act as solvents. Alcohol, ethyl lactate and oxy-1,2-ethanediyl nonylphenyl-omega-hydroxy are preferably included in the remover formulation. The alcohol acts as a solvent and a drying agent. The ethyl lactate acts as a solvent. The oxy-1,2-ethanediyl nonylphenyl-omega-hydroxy acts a surfactant to remove the solvents. The remover formulation also preferably includes aloe vera, propylene glycol and water. The aloe vera and propylene glycol act as moisturizers to replenish moisture removed from the hands by the solvents.

The at least one towellette is preferably contained in the form of a roll, which is retained in a pop-up dispenser. However, other methods of dispensing the at least one towellette may also be used. Each towellette is preferably a scrub towellette. The scrub towel includes a smooth surface formed on one side and a rough surface formed on the other side. A plurality of holes are formed through the scrub towellette to aid in cleaning. The smooth surface is used for cleaning a small amount of unwanted material off the hands and the rough surface is used for cleaning a large amount of unwanted material off the hands.

Although specific components have been disclosed in the remover formulation, the remover formulation should not be limited to those components, but should include any component that may substituted for any of the previously recited component.

Accordingly, it is an object of the present invention to provide a remover formulation, which may be safely used to clean paint, printing inks or adhesives from hands.

It is a further object of the present invention to provide a remover formulation, which may be used to remove nail polish from nails.

Finally, it is another object of the present invention to provide a remover formulation, which does not contain acetate or an acetate derivative.

These and additional objects, advantages, features and benefits of the present invention will become apparent from the following specification.

DETAILED DESCRIPTION OF THE PREFERRED EMBODIMENTS

Figure 2:
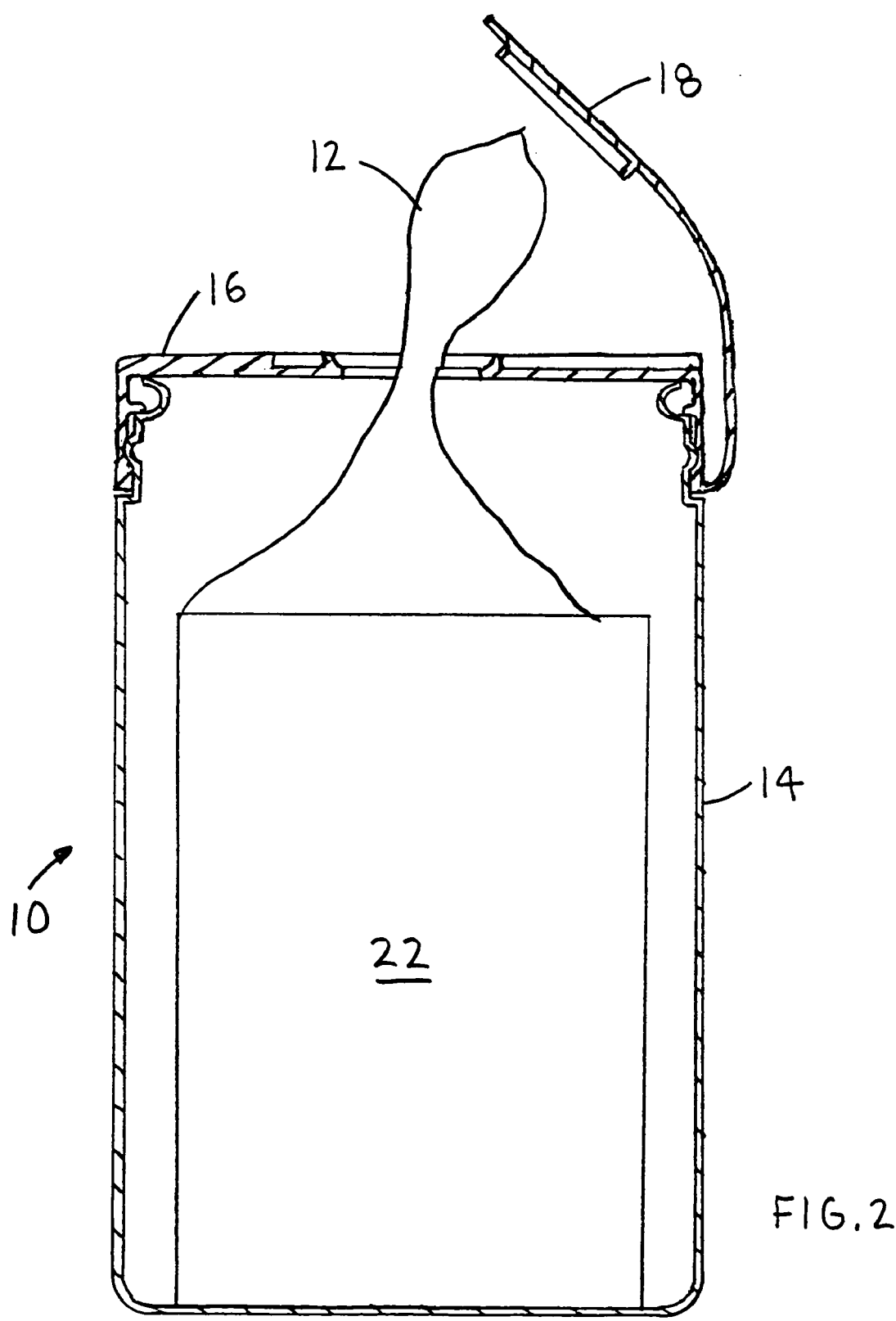
FIG. 2 is a cross-sectional view of a pop-up dispenser with a towellette being dispensed therefrom in accordance with the present invention.

With reference now to the drawings, and particularly to FIG. 2, there is shown a cross sectional view of a pop-up dispenser 10 with at least one towellette 12 contained therein. The pop-up dispenser 10 preferably includes a container 14, a dispenser cap 16 and a cover 18. The cover 18 preferably extends from a side of the dispenser cap 16. The cover 18 snaps on to a top of the dispenser cap 16 to prevent evaporation of the remover formulation from the at least one towellette 12. The dispenser cap 16 is preferably attached to a top of the container 14 with a snap fit. The invention should not be limited to the type of dispenser shown, but include any suitable dispenser.

Figure 1:
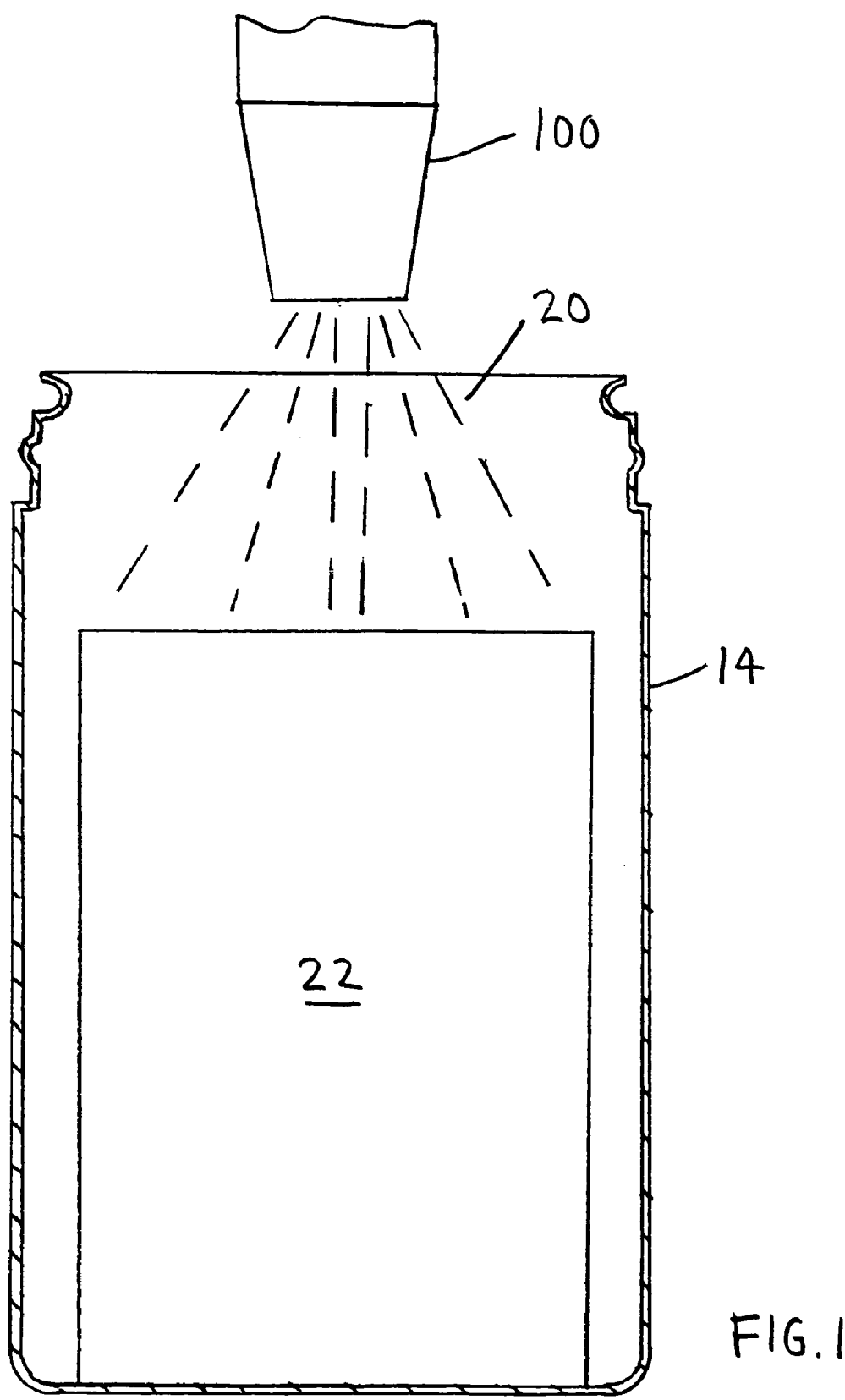
FIG. 1 is a cross-sectional view of a roll of towellettes disposed in a container being sprayed with remover formulation in accordance with the present invention.

With reference to FIG. 1, a roll 22 of towellettes 12 is preferably impregnated with a remover formulation 20, utilizing a spray nozzle 100. Other methods of impregnating the roll 22 may also be used. The pop-up dispenser 10 is well known in the art and may be purchased from one of many companies. However, other methods of dispensing the at least one towellette 12 may also be used. The remover formulation 20 safely cleans paint, printing inks or adhesives from hands. The remover formulation 20 also removes nail polish from nails. The remover formulation 20 does not contain acetate or an acetate derivative.

The remover formulation is applied to the hands or nails with the at least one towellette 12. Each towellette 12 is preferably a scrub towellette. The scrub towellette includes a smooth surface formed on one side and a rough surface formed on the other side. A plurality of holes are formed through the scrub towellette to aid in cleaning. The smooth surface is used for cleaning a small amount of unwanted material off the hands and the rough surface is used for cleaning a large amount of unwanted material off the hands. The remover formulation may also be contained in a spray apparatus, such as a pump spray apparatus or in an aerosol spray apparatus. If the remover formulation is contained in a spray apparatus, the remover formulation would be sprayed on some type of wiping device, such as a paper towel, rag or scrub towellette.

The following remover formulation embodiment describes preferred components for safely removing polyurethane paint, enamel paint, printing inks, adhesives or other unwanted substances from hands, or nail polish from finger nails. The remover formulation includes dimethyl ester, dimethyl sulfoxide and methyl soyate, which all act as solvents. Alcohol, ethyl lactate and Poly (oxy-1,2-ethanediyl), Alpah (nonylphenyl-omega-hydroxy) are preferably included in the remover formulation. The alcohol acts as a solvent and a drying agent. The alcohol is preferably denatured. The ethyl lactate acts as a solvent. The oxy-1,2-ethanediyl nonylphenyl-omega-hydroxy acts a surfactant to remove the solvents. The remover formulation also preferably includes aloe vera, propylene glycol and water. The aloe vera and propylene glycol act as moisturizers to replenish moisture removed from the hands by the solvents. It is also preferable to add a scent.

Preferred percentages of each of the components are disclosed in the below table:

Remover Formulation

| Component | Percent by weight |
| --- | --- |
| Water | 2–15 |
| Alcohol | 5–25 |
| Aloe Vera | 1–5 |
| Ethyl Lactate | 1–15 |
| Dimethyl Ester | 5–63 |
| Dimethyl Sulfoxide | 2–18 |
| Methyl Soyate | 6–26 |
| Poly (oxy-1,2-ethanediyl), Alpah (nonylphenyl-omega-hydroxy) | 2–15 |
| Propylene Glycol | 1–9 |
| Scent | 1–2 |

To produce the remover formulation, the water and alcohol are preferably added to a phase tank and agitated for a period of five minutes. The remaining components are then added to the water and alcohol mixture and agitated for at least an additional 5 minutes.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

What is claimed is:

1. A method of removing unwanted material from hands or nail polish from nails, comprising the steps of:

providing a remover formulation that removes unwanted material from hands or nail polish from nails;

applying said remover formulation to a wiping device;

providing said remover formulation with a dimethyl sulfoxide, a dimethyl ester and a methyl soyate; and wiping at least one hand or at least one nail with said wiping device.

2. The method of removing unwanted material from hands or nail polish from nails of claim 1, further comprising the step of:

retaining a plurality of wiping devices in a roll, retaining said roll for dispensing.

3. The method of removing unwanted material from hands or nail polish from nails of claim 1, further comprising the step of:

retaining said remover formulation in a spray apparatus, spraying said composition on said wiping device.

4. The method of removing unwanted material from hands or nail polish from nails of claim 1, further comprising the step of:

providing said remover formulation with an alcohol.

5. The method of removing unwanted material from hands or nail polish from nails of claim 1, further comprising the step of:

providing said remover formulation with an ethyl lactate.

6. The method of removing unwanted material from hands or nail polish from nails of claim 1, further comprising the step of:

providing said remover formulation with a surfactant.

7. A method of removing unwanted material from hands or nail polish from nails, comprising the steps of:

providing a remover formulation that removes unwanted material from hands or nail polish from nails;

spraying a roll of wiping devices with said remover formulation;

providing said remover formulation with a dimethyl sulfoxide, a dimethyl ester and a methyl soyate;

retaining said roll for dispensing;

removing at least one wiping device from said roll; and wiping at least one hand or at least on nail with said wiping device.

8. The method of removing unwanted material from hands or nail polish from nails of claim 7, further comprising the step of:

providing said remover formulation with an alcohol.

9. The method of removing unwanted material from hands or nail polish from nails of claim 7, further comprising the step of:

providing said remover formulation with an ethyl lactate.

10. The method of removing unwanted material from hands or nail polish from nails of claim 7, further comprising the step of:

providing said remover formulation with a surfactant.

* * * * *